(12) United States Patent
Wissman

(10) Patent No.: US 7,255,770 B2
(45) Date of Patent: Aug. 14, 2007

(54) METHOD FOR LASER WELDING FLEXIBLE POLYMERS

(75) Inventor: Lawrence Y. Wissman, Santa Barbara, CA (US)

(73) Assignee: Mentor Corporation, Santa Barbara, CA (US)

( * ) Notice: Subject to any disclaimer, the term of this patent is extended or adjusted under 35 U.S.C. 154(b) by 0 days.

(21) Appl. No.: 10/217,494

(22) Filed: Aug. 12, 2002

(65) Prior Publication Data

US 2004/0030384 A1 Feb. 12, 2004

(51) Int. Cl.
*B29C 65/00* (2006.01)
*A61F 2/12* (2006.01)

(52) U.S. Cl. ................ 156/304.2; 623/901; 623/8

(58) Field of Classification Search ............. 156/71, 156/182, 158, 304.2, 304.3, 272.8, 272.2, 156/379.8; 623/7, 8, 11.11, 23.64, 901; 249/121.63, 249/121.64; 428/35.2, 198, 352
See application file for complete search history.

(56) References Cited

U.S. PATENT DOCUMENTS

| | | | | |
|---|---|---|---|---|
| 4,029,535 A | * | 6/1977 | Cannon et al. | 156/272.8 |
| 4,046,947 A | * | 9/1977 | Brodie | 428/352 |
| 4,127,761 A | | 11/1978 | Pauley et al. | 219/121 |
| 4,636,609 A | * | 1/1987 | Nakamata | 219/121.64 |
| 4,857,697 A | * | 8/1989 | Melville | 219/121.63 |
| 5,151,149 A | * | 9/1992 | Swartz | 156/379.8 |
| 5,294,376 A | | 3/1994 | Byker | 252/600 |
| 5,662,708 A | * | 9/1997 | Hayes et al. | 623/8 |
| 6,074,421 A | * | 6/2000 | Murphy | 623/8 |
| 6,083,584 A | * | 7/2000 | Smith et al. | 428/35.2 |
| 6,203,570 B1 | * | 3/2001 | Baeke | 623/8 |
| 6,295,714 B1 | * | 10/2001 | Roychowdhury et al. | 29/516 |
| 6,315,796 B1 | * | 11/2001 | Eaton | 623/8 |
| 6,537,402 B2 | * | 3/2003 | Pate et al. | 156/71 |
| 6,565,595 B1 | * | 5/2003 | DiCaprio et al. | 623/1.11 |
| 6,586,080 B1 | * | 7/2003 | Heifetz | 428/198 |
| 6,596,122 B1 | * | 7/2003 | Savitski et al. | 156/304.2 |
| 6,676,790 B1 | * | 1/2004 | Valentinsson et al. | 156/182 |

FOREIGN PATENT DOCUMENTS

| | | |
|---|---|---|
| EP | 0 281 347 B1 | 2/1988 |
| EP | 0 495 655 B1 | 1/1992 |
| EP | 0 721 024 B1 | 12/1995 |
| WO | WO 00/20157 | 4/2000 |

OTHER PUBLICATIONS

Puetz et al., "Laser Welding Offers Array of Assembly Advantages" Modern Plastics International, pp. 127-130, Sep. 1997.
Weber "Welding with Light," Assembly Jan. 2002, pp. 34-43.
Shah "Polyurethane Thin-Film Welding for Medical Device Applications," Medical Device & Diagnostic Industry Sep. 2002, pp. 62-68.

\* cited by examiner

*Primary Examiner*—David J. Isabella
(74) *Attorney, Agent, or Firm*—Fish & Richardson P.C.

(57) ABSTRACT

The present invention concerns methods for joining flexible polymer workpieces using light energy. These methods, referred to as laser welding, can be used to join thermoplastic or thermoset polymers. The laser welding method of the invention is applicable to the creation or repair of any article requiring the bonding of two flexible polymer components or a flexible polymer component and an inflexible polymer component.

37 Claims, 3 Drawing Sheets

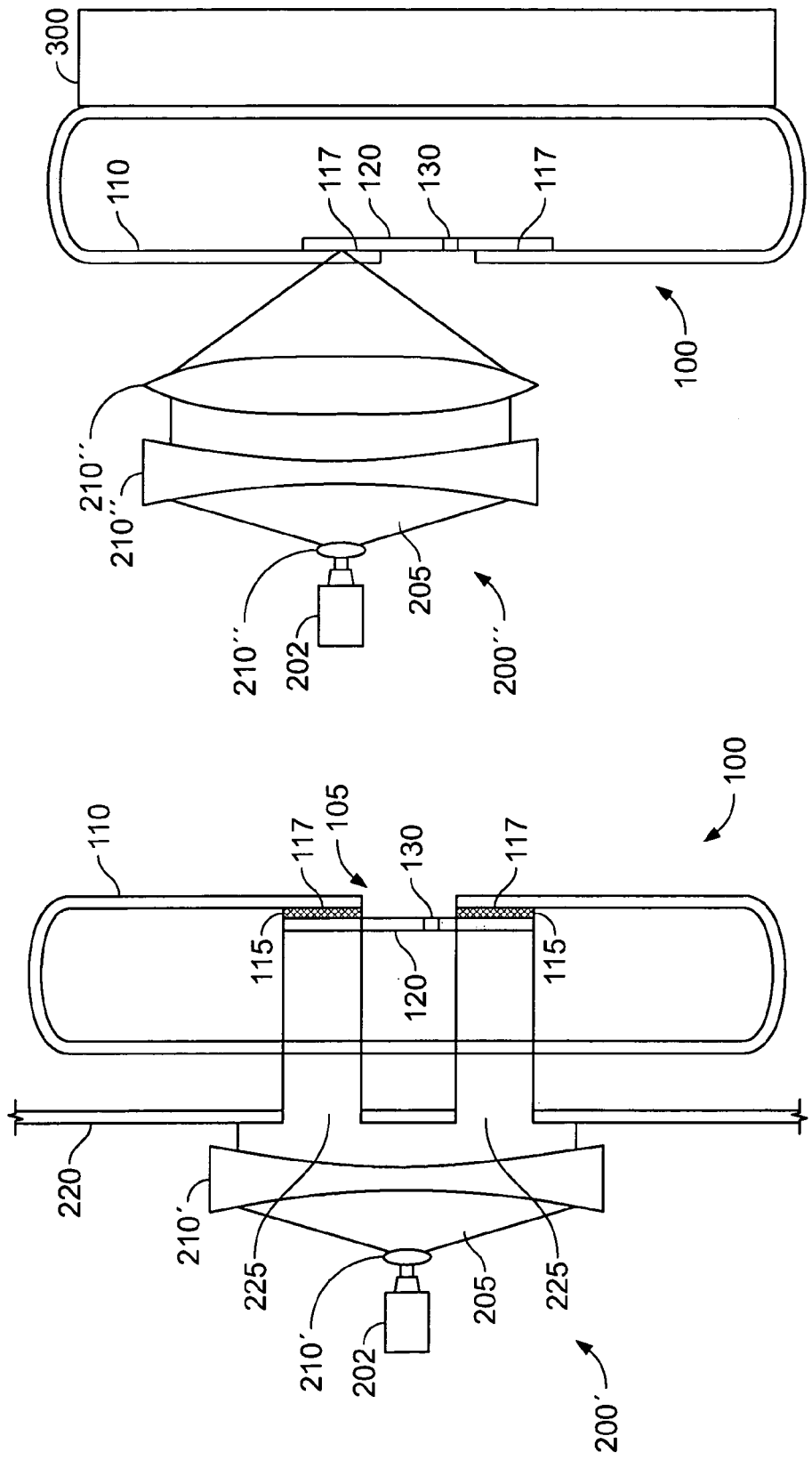

METHOD FOR LASER WELDING FLEXIBLE POLYMERS

TECHNICAL FIELD

This invention relates to methods for bonding thermoplastic and thermoset polymers. More particularly, this invention related to methods for bonding such materials with light energy.

BACKGROUND

The robust bonding of plastic materials is useful in the manufacture of many devices. Many devices, for example, medical devices, can have challenging bond requirements in terms of strength, durability, flexure, and permeability. It has been a particular challenge to satisfy applications involving bonding of elastomers, which are conventionally defined as polymeric materials able to be elongated at least 100% without experiencing yield or other failure. In many instances the difficulty lies in forming a bond that has the strength, flexibility, and integrity of the material adjacent to the bonded area. In addition, it is important to provide a bonded area that exhibits resistance to fatigue and polymer fracture failure. Because of this, bonded elastomers in which the bonded area is the same as the components being bonded can outperform alternative bonding methods.

Elastomeric polymers can be bonded with adhesives. However, it can be difficult to identify an adhesive that provides a strong bond between components formed of elastomeric materials. Typical adhesives capable of bonding elastomeric polymers with sufficient strength often fail to form a lasting bond because the mechanical properties of the adhesives generally do not match the mechanical properties of the elastomeric components which they join.

In an alternative approach, elastomeric components can be bonded by application of conductive heat and pressure to the region to be bonded. Such bonding is commonly achieved by holding together the components to be bonded and pressing them between heated platens. The platens are typically metallic, and it is therefore difficult or impossible to monitor the position of the components or the completeness of the bond during bonding. Defects are common and difficult to avoid. Moreover, due to manufacturing requirements, there are often long periods during which the platens must be held at high temperature, but are not being actively used for bonding. This can consume considerable energy and can pose burn risks for personnel operating the bonding equipment.

Components formed of thermosetting polymers such as synthetic rubber can be bonded by placing uncured polymer material between the components and then vulcanizing the uncured polymer material. In many cases this vulcanization bonding process entails the use of heated platens and thus entails the difficulties outlined above. Moreover, where the composition of the uncured polymer material is not identical to that of the components being bonded, the dissimilarity in mechanical properties can lead to failure of the bond.

Ultrasound and RF bonding can be used to join polymeric components. However, like heat sealing and vulcanization bonding, these bonding methods generally employ opaque, metal platens that interfere with observation of the alignment and layout of the components during bonding.

Ultrasonic welding can be used to bond polymeric components. To be effective, the ultrasonic waves must be transmitted through a rigid plastic material to an energy director zone in contact with another rigid plastic material. Energy dissipation occurs through conversion of the ultrasound vibrational energy to heat at the interface, where bonding occurs.

Friction or spin bonding is sometimes used to bond polymeric components, but these techniques are not suitable where static positioning of the components is required for considerations such as proper fit, alignment, and orientation of the components.

Staking and similar attachment methods using fastening devices such as screws, bolts, rivets and the like generally do not provide hermetic seals without the addition of gasket materials which require frames, brackets or similar support, defeating the intent of bonding without the use of additional extraneous material. Moreover, the use of additional materials to either form or seal the joint can lead to failure arising from the dissimilar mechanical properties of the materials used.

SUMMARY

The present invention concerns methods for joining flexible polymer workpieces using light energy. These methods, referred to as laser welding, can be used to join thermoplastic or thermoset polymers. The laser welding method of the invention is applicable to the creation or repair of any article requiring the bonding of two flexible polymer components. Among the polymers that can be bonded using the methods of the invention are: silicone, polyurethane, silicone-polyurethane co-polymers, flexible polyvinyl chloride (PVC), and thermoplastic elastomers such as polymers of aliphatic and substituted or branched aliphatic esters of acrylic and methacrylic acid.

The methods of the invention bond components formed of thermoset or thermoplastic polymers by exposing the region to be bonded to light energy, preferably light energy generated by a laser. The light energy applied to the region of the bond is absorbed by the polymer itself or by an absorbing material applied to or integrated into one or both of the polymer components. In the case of thermoplastic polymers, the absorbed light energy heats the polymer material sufficiently to melt or simply soften the polymer material such that a bond is formed between the components. In the case of thermoset polymers, the absorbed light energy heats the polymer material sufficiently to cause a chemical reaction that results in the formation of a bond between the components. Both the wavelength of the light energy applied and the total amount of energy applied are chosen such that sufficient energy is absorbed by the absorbing material or the polymer itself to create an adequate bond between the components.

The methods of the invention are particularly useful in the manufacture of medical devices. For, example, the methods are useful in the manufacture of prostheses to create fluid tight bonds such as are used in bonding dilation and fixation balloons to catheters, sealing lumens of inflatable devices and prostheses, urine and ostomy bag seams, and tubing and connector assemblies. The methods can be applied to prostheses formed of any thermoplastic or thermoset polymer. More generally, the present invention provides methods for laser welding components comprising flexible polymers such as polyurethane, PVC, acrylic and silicone.

The invention features a method for bonding a first workpiece to a second workpiece, the method including: providing a first workpiece comprising a flexible polymer comprising portion; providing a second workpiece comprising a flexible polymer comprising portion; contacting the first and second workpieces such that an overlap region comprising a region of the flexible polymer comprising portion of the first workpiece and a region of the flexible polymer comprising portion of the second workpiece is formed; and exposing at least a portion of the overlap region to light of a selected wavelength in an amount adequate to heat the light exposed portion sufficiently to bond the flexible polymer comprising portion of the first workpiece to the flexible polymer comprising portion of the second workpiece.

In various embodiments at least a portion of the flexible polymer comprising portion of either the first workpiece or the second workpiece or both comprises a light absorbing substance that absorbs light of the selected wavelength; the light absorbing substance is coated on a portion of the surface of the flexible polymer comprising portion of either the first workpiece or the second workpiece or both; the light absorbing substance is incorporated into the flexible polymer portion of either the first workpiece or the second workpiece or both; the flexible polymer comprises a thermoset polymer; the first workpiece and the second workpiece are subjected to heat treatment subsequent to bonding; the first workpiece and the second workpiece are subjected to heat setting subsequent to bonding; the flexible polymer comprises a thermoplastic polymer; the light is provided by a laser; the polymer comprises silicone; and the polymer comprises polyurethane.

The invention also features a method for forming a sealed prosthesis, the method including: providing a flexible polymeric shell having an opening, the shell having an inner and outer surface; providing a flexible polymeric patch covering the opening and overlapping the shell such that an overlap region comprising a portion of the patch and a portion of the shell is formed; and exposing at least a portion of the overlap region to light of a selected wavelength in an amount adequate to heat the light exposed portion sufficiently to bond the patch to the shell thereby forming a sealed prosthesis.

In various embodiments of the method for forming a sealed prosthesis, the light is supplied by a laser; the shell and the patch comprise a thermoplastic polymer; the shell and the patch comprise a thermoset polymer; the shell and the patch comprise high temperature vulcanization silicone; the patch comprises high temperature vulcanization silicone and shell comprises room temperature vulcanization silicone; the patch comprises room temperature vulcanization silicone and the shell comprises high temperature vulcanization silicone; the patch and the shell comprise room temperature vulcanization silicone; the shell and patch comprise polyurethane; the shell and patch have a thickness between about 0.010 inches and about 0.0005 inches; the prosthesis is a mammary prosthesis; the shell is made from room temperature vulcanization silicone and the patch is made from high temperature vulcanization silicone; the method further comprises providing a light absorbing substance disposed in the overlap region which substance absorbs light of the selected wavelength thereby heating the surfaces of the patch and shell in contact with each other. In certain embodiments, the method includes providing a light absorbing material disposed on either the surface of the patch or the surface of the shell in the overlap between the patch and shell. In some embodiments the light absorbing material is integrated into an absorber patch that is disposed in the overlap and the light absorbing substance is carbon black.

The invention also features a prosthesis comprising: a shell having an opening, the shell having an inner and outer surface; a patch covering the opening and overlapping the shell such that an overlap region is formed; and a bond formed at the overlap between the shell and the patch wherein the bond is formed by heating the surfaces of the shell and the patch in the overlap region with light energy (e.g., a laser). In various embodiments the shell and patch are made from polyurethane; the prosthesis is a mammary prosthesis; the shell and patch are made from thermoset polymers; the shell and patch are made from high temperature vulcanization silicone; and the shell and patch are made from room temperature vulcanization silicone.

The invention features a prosthesis comprising: a polyurethane shell; a polyurethane patch; and a bond at an overlap between the shell and the patch forming an enclosed lumen. The shell and the patch of the prosthesis can have thickness in the range of about 0.0005 inches to about 0.010 inches.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 4 depicts an apparatus that laser welds components to form a prosthesis.

FIG. 5 depicts an apparatus that laser welds components to form a prosthesis.

Like reference symbols in the various drawings indicate like elements.

DETAILED DESCRIPTION

Described below are methods for bonding two flexible polymer workpieces using light energy. The methods are applicable to most flexible polymers and in particular to elastomeric polymers. The description of the bonding methods is followed by a description of the application of the methods to forming prostheses, e.g., a mammary prosthesis, from flexible polymer components.

EXAMPLE 1

Figure 1:
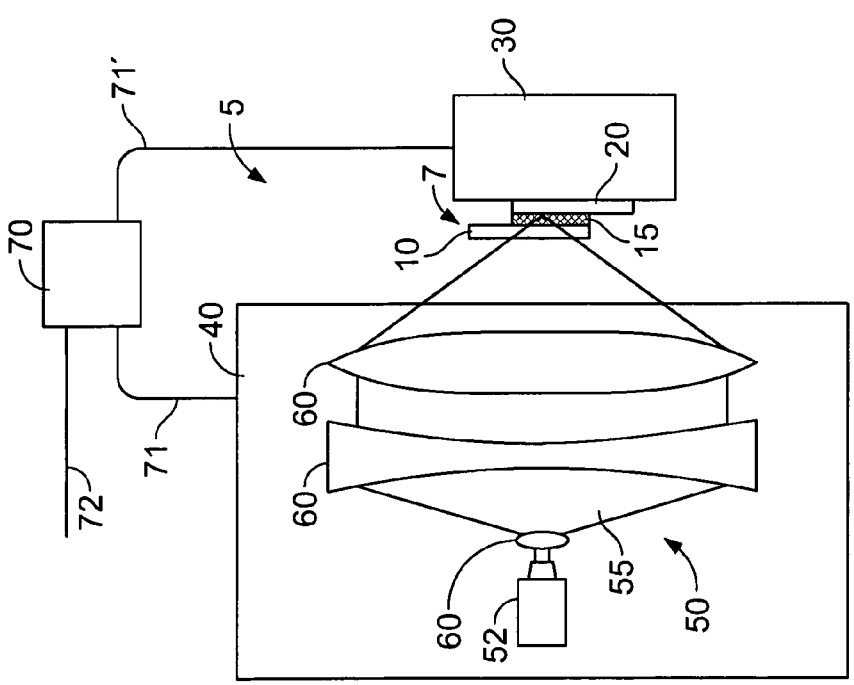
FIG. 1 depicts an apparatus that joins two polymeric components using light energy.

FIG. 1 shows an apparatus 50 suitable for using light energy to bond two flexible polymer workpieces to form a unitary workpiece 7. The unitary workpiece 7 is formed from a first workpiece 10, a second workpiece 20, and an absorber patch 15 all formed of flexible thermoplastic polymer. In this embodiment, the absorber patch 15 is coated on both sides with a light absorbing substance. In other embodiments the light absorbing substance is dispersed throughout the absorber patch.

The unitary workpiece is formed using an apparatus 50 that includes a laser light source 52 and an optics system 60 that focuses the laser light onto the first and second workpieces in the region of absorber patch 15. The apparatus 50 also includes an light source stage 40 that holds the light source and optics. The apparatus 50 also includes a workpiece stage 30 that holds the first and second workpieces and absorber patch. Relative movement of the light source stage 40 and the workpiece stage 30 allows light energy to be applied to any desired region of the first and second workpieces, e.g., the region defined by the absorber patch.

Prior to bonding, the first workpiece and the second workpiece are held in contact with the absorber patch. Is this embodiment, the absorber patch defines the region to be bonded. When light energy is applied to the region of the absorber patch, the light absorbing substance coated on the absorber patch absorbs the light from the source 52 thereby heating the absorber patch 15 and the surfaces of the first workpiece 10 and the second workpiece 20 in contact with the absorber patch. Such local heating softens the absorber patch polymer and the polymer of the workpieces thereby producing bonds between the first workpiece 10 and the absorber patch 15 and between the second workpiece 20 and the absorber patch 15, effectively indirectly bonding the two workpieces to each other.

In some embodiments, the absorber patch is preassembled with one of the two workpieces prior to final assembly on the stage 30. In other embodiments, the absorber patch is not used and instead a light absorbing substance is coated on or integrated into one or both workpieces in the region to be bonded, e.g., within the entire region of contact between the two workpieces.

The light absorbing substance must be able to absorb energy from the light produced by the laser source, and the components lying between the light source and the light absorbing substance must be sufficiently transparent to the light produced by the laser source for sufficient light to reach the light absorbing substance. Thus, at least in the region to be bonded, the polymer components allow at least some transmission of the laser light in the wavelength range absorbed by the light absorbing substance.

The apparatus 50 further includes control and monitoring system 70 with control lines 71 and 71'. The control system controls the position of the stages 40 and 30 and also controls the output of the laser source 52. The control system 70 receives instructions from instruction line 72. In some embodiments, the control system 70 is a mechanical device responding to inputs from an operator overseeing the welding process. In other embodiments, the control system 70 is an electronic system.

In some embodiments, an aiming means, such as co-axial Helium-Neon lasers are used for alignment and monitoring of the process. In some embodiments, vision systems using, for example, charge coupled device (CCD) cameras and viewing monitors, recording systems are used to monitor the welding process. In some embodiments, computer and/or programmable logic control (PLC) systems control the beam for precision, efficiency, and reproducibility of the weld. Furthermore, such control allows for the automatic bonding of various sizes, shapes and types of products.

EXAMPLE 2

Figure 2A:
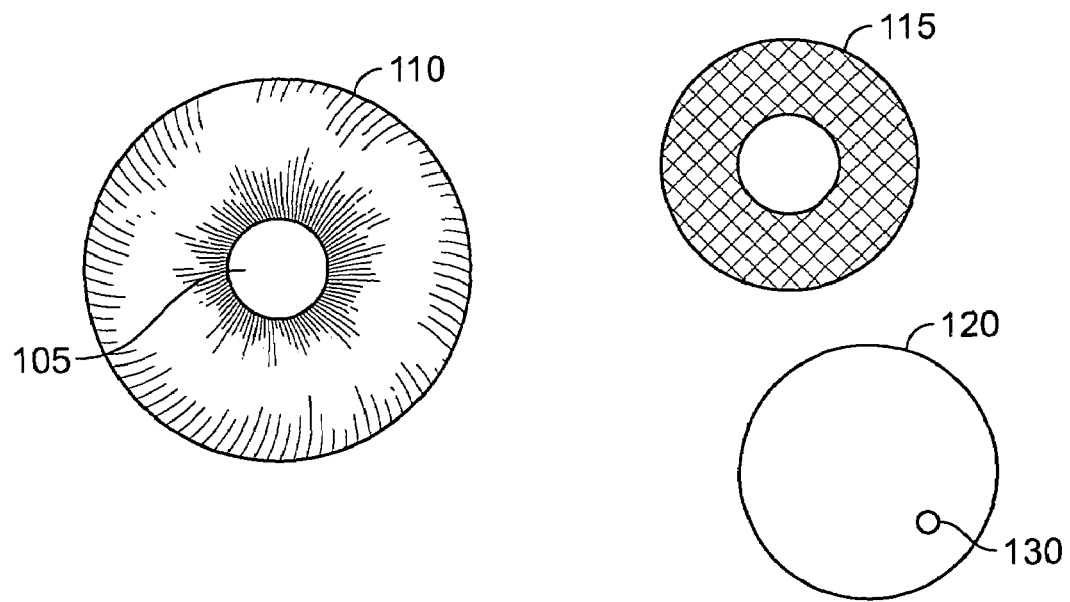
FIG. 2A depicts certain components used to make a prosthesis.

FIG. 2A shows certain components used to make a prosthesis 100 according to one embodiment of the invention. The components include a shell 110, a sealing patch 120, and an absorber patch 115. The polymers that make up these components preferably meet certain criteria. They are generally biocompatible. They are stable in the presence of a fill material, and the fill material diffuses negligibly slowly or not at all through the prosthesis material. The polymers are selected such that the implanted prosthesis resists failure and rupture due to both tissue abrasion and self-abrasion. The components, particularly the shell, are generally thin and quite flexible so that the implanted prosthesis is tactilely and visually natural. Two types of polymers that include materials which meet these criteria are thermoset polymers such as high temperature vulcanization (HTV) silicone and room temperature vulcanization (RTV) silicone and thermoplastic polymers such as polyurethane.

Shell 110 is formed from HTV silicone using dip molding. An appropriately sized and shaped mandrel is dipped into a silicone dispersion and then removed to allowed partial cure of the silicone. Repeating this process adds additional layers of polymer onto the mandrel. The process is completed when a shell having a desired thickness has been built up on the mandrel. The finished shell 110 is then cured as necessary and removed from the mandrel.

The dip molding process leaves an opening 105 in the shell 110. In order to form an enclosed and sealed prosthesis, a sealing patch 120 formed of HTV silicone is used to close opening 105. The sealing patch is commonly fitted with a fill port 130. This fill port is used to introduce filling material into the prosthesis after the prosthesis is formed and sealed.

An absorber patch 115 is used to join the sealing patch 120 to the shell 110. The absorber patch 115 is placed between sealing patch 120 and shell 110. The absorber patch 115 is formed from uncured HTV silicone. A suitable light absorbing substance is applied to the surfaces of the absorber patch 115. The light absorbing substance is a substance that absorbs energy in a wavelength range emitted by the laser used in the laser welding step.

The substantial material homogeneity of the sealing patch, absorber patch, and shell reduces the potential for large gradients in the mechanical properties of the completely formed prosthesis. Variations in mechanical properties are not desirable because the variation can induce some portions of the formed prosthesis to flex, compress or elongate more or less than their surroundings. Such joints can typically act as nucleation sites for mechanical failure. The shell and sealing patch are generally about 0.0005 inches to about 0.20 inches, preferably about 0.005 inches to about 0.1 inches, even more prefereably about 0.010 inches to about 0.040 inches, thick. Furthermore, the absorber patch is generally about 0.0005 to about 0.010 inches thick. The relative thinness of the shell is an important aesthetic factor since, without significant soft tissue coverage, it can be felt through skin.

Figure 2B:
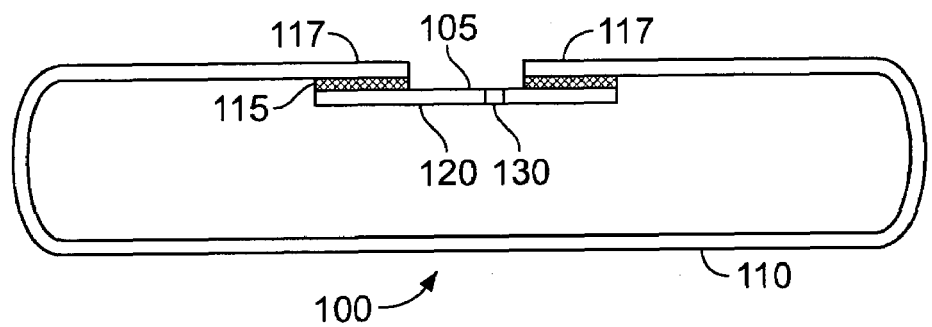
FIG. 2B depicts a cross section of an assembled prosthesis.

In order to form the prosthesis, the shell 110, the sealing patch 120 and the absorber patch 115 are assembled as shown FIG. 2B. The sealing patch 120 covers the opening 105 creating an overlap region 117 between the sealing patch and the shell. The absorber patch 115 is shaped to fill the overlap region 117, and it is placed between the sealing patch and the shell as shown. The bonds between these components are formed by heating the absorber patch using light energy. The absorber patch is in thermal contact with the inner surface of a portion of the shell and the outer surface of a portion of the sealing patch. Thus, these surfaces are heated enough to form a bond with the absorber patch.

As noted above, the absorber patch includes a light absorbing compound that absorbs light in a wavelength range emitted by the laser. The light absorbing compound can be incorporated directly into the absorber patch as it is made. In other embodiments, the laser-absorbing compound can be applied to the surface of the absorber patch prior to assembly; for example, a suspension containing the laser-absorbing compound can be painted onto the surfaces of the absorber patch. The suspension fluid is allowed to evaporate leaving the surfaces of the absorber patch coated with laser absorbing compound. Carbon black is a suitable laser-absorbing compound. In other embodiments, pigments, lakes, dyes such as the FD&C colors or other dyes can be used. In another embodiment, the absorbing patch can be bonded onto the surface of the shell or the patch prior to the full assembly of the prosthesis.

While in this embodiment, the sealing patch and the absorber patch are placed inside the shell, they can also be placed outside the shell.

In the case of thermoset polymers, it can be desirable to further treat the material after bonding to completely cure the material and/or eliminate catalyst residue. Thus, it can be desirable to simply heat the material, e.g., in a conventional oven, and/or subject the material to heat setting or stress relief heat treatment after bonding.

EXAMPLE 3

Figure 3:
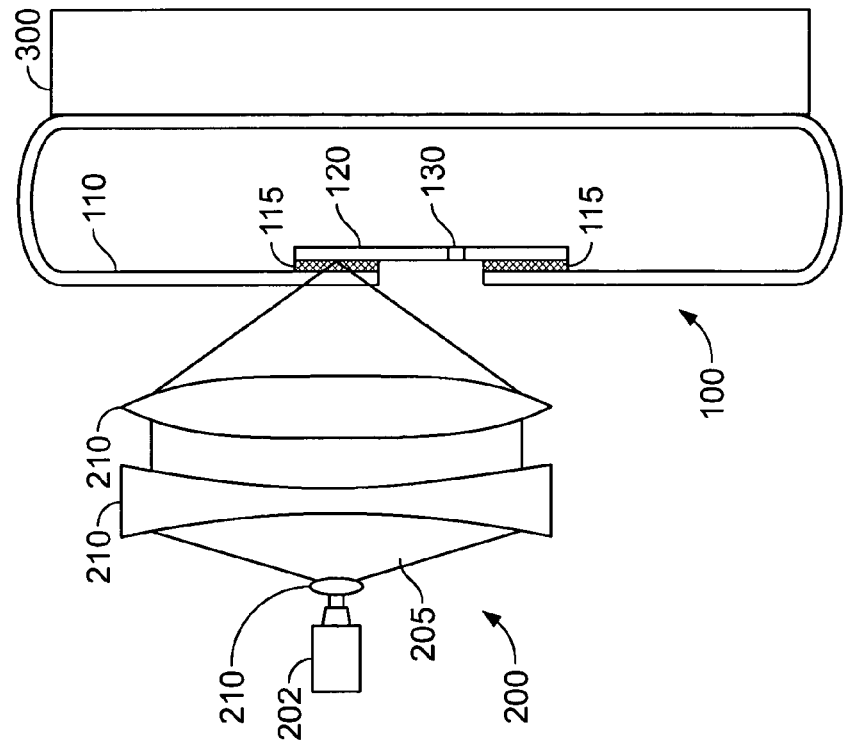
FIG. 3 depicts an apparatus that laser welds components to form a prosthesis.

FIG. 3 is a schematic depiction of an apparatus suitable for laser welding the prosthesis assembly depicted in FIG. 2B.

The shell 110, sealing patch 120, and absorber patch 115 are assembled on a stage 300 in a laser welding apparatus 200 as shown. The laser welding apparatus includes a laser light source 202 and an optics system 210 that focuses the laser light onto the absorber patch 115. The stage 300 moves relative to the focus of the laser light forming the secure weld of patch 120 to shell 110.

The wavelength of the laser light 202 is chosen to provide laser energy in the absorption range of the light absorbing substance. Thus, exposing the light absorbing substance to light produced by the laser effectively heats the absorber patch. Thermal energy is transferred from the absorber patch to the adjoining surface of the sealing patch and to the adjoining surface of the shell. This heating of the surfaces of the sealing patch and the shell causes the formation of a bond between the absorber patch and the shell and between the absorber patch and the sealing patch, effectively sealing the lumen of the shell.

Laser 202 is a diode laser with a wavelength between about 800 and 1100 nm. About 20-30 Watts is generally useful, however more or less power may be desired depending on the size of the area to be welded and the desired speed of processing. Further, adjustments common to laser control systems and launch optics control flux and flux density.

Other embodiments use other types of lasers such as an Nd: YAG laser. Furthermore, other non-laser light sources can be employed. In such cases an optic system can also include optical filtering elements to modify the raw spectral output from a light source (for example an arc light) such that light is preferentially absorbed only in the region to be welded and does not inadvertently heat or damage or weld other portions of the prosthesis. The light absorbing substance is matched to the light source such that it absorbs energy in a wavelength range emitted by the light source.

In some embodiments, the absorber patch 115 can be omitted. Instead, the laser absorbing material is applied directly to either the surface of the shell or the surface of the patch or both surfaces in the overlap region. Alternatively, the absorbing material can be introduced into the overlap region of the shell or sealing patch by suspending the absorbing material in the final bath of the polymer dispersion used in the last layer of dip molding. Regions that are not to be provided with absorbing material are appropriately shielded. Bonding of thermoset materials is done by the effect of the laser on uncured material.

EXAMPLE 4

In some embodiments, the optics system does not focus the laser light to a point but rather the optic system produces a wide beam suitable for flooding the entire weld area simultaneously with laser light.

FIG. 4 depicts an apparatus 200' suitable for bonding a sealing patch to a prosthesis shell 100 using a laser flood. The shell 110, sealing patch 120, and absorber patch 115 of prosthesis 100 are assembled in a laser welding apparatus 200' as shown. The laser welding apparatus includes a laser light source 202 and an optics system 210' that guides laser light 205 from the laser onto mask 220. The light passes through openings 225 of mask 220 and is incident on the absorber patch 115 after passing through sealing patch 120. The openings are positioned so that only the overlap region 117 where the sealing patch and the shell overlap is illuminated.

EXAMPLE 5

In certain embodiments, there is no need for an applied absorbing substance because the components being bonded themselves absorb sufficient light energy to permit formation of an acceptable bond. FIG. 5 depicts a laser welding apparatus 200" that includes laser 202 and optic system 210". Optic system 210" focuses the laser light 205 to a well-defined focus. The assembled prosthesis is positioned on a movable stage 300 as shown. The focused laser beam produces a large spatial gradient in light intensity and even in the absence of an absorbing material, the properly focused laser beam locally heats and bonds the polymer material near the light focus which at the contact point between the shell and the sealing patch within the overlap region 117. By translation of the stage 300, the entire overlap region between the shell and patch or at least a continuous seal around the opening 105 is bonded.

EXAMPLE 6

An elastomeric shell is formed by conventional dip-molding in a silicone dispersion using an appropriately sized and shaped mandrel. The shell has an opening on its posterior face in order to strip it off the mandrel. The opening in the posterior face of the shell is sealed using a sealing patch formed of silicone sheeting. The patch is shaped and sized to be somewhat larger than the opening in the posterior face of the shell. The patch is positioned inside the shell such that the perimeter of the patch overlaps the edge of the shell surrounding the opening. An absorber patch of uncured HTV silicone is placed between the shell and sealing patch.

Carbon black, which serves as a light absorbing substance, is incorporated into the absorber patch. Alternatively, some other substance that absorbs light in the in the 800+ nm range can be used. A diode or Nd YAG laser outputting 20-30 Watts of power is used to heat the overlap region to 120° C. to 175° C. and the weld is formed. The shell is subsequently heat treated to fully cure the absorber patch. In some cases, the laser welding process itself, by virtue of the heat created, will be sufficient to fully cure any uncured or partially cured material in the bond region.

EXAMPLE 7

An elastomeric shell is formed by dip-molding polyurethane using an appropriately sized and shaped mandrel. The shell has an opening on its posterior face in order to strip it off the mandrel. The opening in the posterior face of the shell is sealed using a sealing patch comprising a polyurethane sheeting. The sealing patch is shaped and sized to be somewhat larger than the opening in the posterior face of the shell. The sealing patch is positioned inside the shell such that the sealing patch faces outward and the perimeter of the sealing patch overlaps the edge of the shell surrounding the opening, forming an overlap region. A polyurethane shell can be 0.0005 inches to 0.10 inches, preferably 0.001 inches to 0.050 inches, more preferably 0.002 inches to 0.015 inches, thick.

The absorber patch is coated on one or both sides with carbon black. A diode or Nd YAG laser outputting 20-30 Watts of power heats the weld region to 120° C. to 225° C. and the weld is formed.

OTHER EMBODIMENTS

In addition, some embodiments involve applying pressure to the components being bonded. Such pressure is useful in forming the bond between the two workpieces and the absorber patch (if used). Typically such pressure is applied with a clear rigid material such as a glass bar or a clear polymer bar. The material is chosen to have minimal absorption of both the laser light and visible light. Such a material can apply external pressure while allowing the laser and visible light to pass through. This enables the operator to form the bond while observing the positioning of the components.

In the case of a prosthesis, after the shell and the sealing patch are bonded, the enclosed shell can be pre-filled or intraoperatively filled through a small fill port with saline, gel, foam, or combinations of these materials or other suitable material known in the art to provide a complete fluid-filled prosthesis. The fill port or valve is sealed or closed, and the prosthesis is sterilized.

The prosthesis can have a single lumen or multiple lumens. It can be formed of silicone rubber, a laminate of various forms of silicone, silicone copolymers, silicone polyurethane copolymers, polyurethane, and various other soft plastics and elastomers in various combinations. Various materials are described in U.S. Pat. Nos. 4,592,755 and 4,205,401. The shell can be filled with a fluid or gel. In addition, an amount of solid material can be combined with the fluid or gel to adjust the density or compressibility of the filling. The prosthesis of the invention can be provided as a kit with a shell and a means for filling the shell, e.g., a syringe. The kit can further include an adapter tube for connecting the syringe to the filling port of the shell.

A number of embodiments of the invention have been described. Nevertheless, it will be understood that various modifications may be made without departing from the spirit and scope of the invention.

What is claimed is:

1. A method for bonding a first workpiece to a second workpiece, the method comprising:
    providing a first workpiece comprising an elastomeric polymer comprising portion;
    providing a second workpiece comprising an elastomeric polymer comprising portion;
    contacting the first and second workpieces such that an overlap region comprising a region of the elastomeric polymer comprising portion of the first workpiece and a region of the elastomeric polymer comprising portion of the second workpiece is formed; and
    after said contacting, exposing at least a portion of the overlap region to light of a selected wavelength in an amount adequate to heat the light exposed portion sufficiently to bond the clastomerie polymer comprising portion of the first workpiece to the elastomeric polymer comprising portion of the second workpiece.

2. The method of claim 1 wherein at least a portion of the elastomeric polymer comprising portion of either the first workpiece or the second workpiece or both comprises a light absorbing substance that absorbs light of the selected wavelength.

3. The method of claim 2 wherein the light absorbing substance is coated on a portion of the surface of the elastomeric polymer comprising portion of either the first workpiece or the second workpiece or both.

4. The method of claim 2 wherein the light absorbing substance is incorporated into the elastomeric polymer portion of either the first workpiece or the second workpiece or both.

5. The method of claim 1 wherein the elastomeric polymer comprises a thermoset polymer.

6. The method of claim 5 further comprising heat treating the first workpiece and the second workpiece subsequent to bonding.

7. The method of claim 5 further comprising heat setting the first workpiece and the second workpiece subsequent to bonding.

8. The method of claim 1 wherein the elastomeric polymer comprises a thermoplastic polymer.

9. The method of claim 1 wherein the light is provided by a laser.

10. The method of claim 1 wherein the polymer comprises silicone.

11. The method of claim 1 wherein the polymer comprises polyurethane.

12. A method for forming a sealed prosthesis, comprising:
    providing an elastomeric polymer shell having an opening, the shell having an inner and outer surface; providing an elastomeric polymer patch covering the opening and overlapping the shell such that an overlap region comprising a portion of the patch and a portion of the shell is formed; and
    after forming said overlap region, exposing at least a portion of the overlap region to light of a selected wavelength in an amount adequate to heat the light exposed portion sufficiently to bond the patch to the shell thereby forming a sealed prosthesis,
    wherein the elastomeric polymer shell comprises a thermoset polymer, and wherein the elastomeric polymer patch comprises a thermoset polymer.

13. The method of claim 12 wherein the light is supplied by a laser.

14. The method of claim 12 wherein the patch and the shell comprise high temperature vulcanization silicone.

15. The method of claim 12 wherein the patch and the shell comprise room temperature vulcanization silicone.

16. The method of claim 12, wherein the shell and patch have a thickness between about 0.1 inches and about 0.005 inches.

17. The method of claim 12 wherein the prosthesis is a mammary prosthesis.

18. The method of claim 12 wherein the shell is made from room temperature vulcanization silicone and the patch is made from high temperature vulcanization silicone.

19. The method of claim 12 further comprising providing a light absorbing substance disposed in the overlap region and wherein the light absorbing substance absorbs light of the selected wavelength, thereby heating the surfaces of the patch and shell in contact with each other.

20. The method of claim 12 further comprising providing a light absorbing material disposed on either the surface of the patch or the surface of the shell in the overlap between the patch and shell.

21. The method of claim 12 wherein the light absorbing material is integrated into an absorber patch that is disposed in the overlap.

22. The method of claim 19 wherein the light absorbing substance is carbon black.

23. A method for forming a sealed prosthesis, comprising:
   (a) providing an elastomeric shell having an opening, the shell having an inner and outer surface;
   (b) providing an elastomeric patch covering the opening and overlapping the shell such that an overlap region comprising a portion of the patch and a portion of the shell is formed; and
   (c) after forming said overlap region, exposing at least a portion of the overlap region to light of a selected wavelength in an amount adequate to heat the light exposed portion sufficiently to bond the patch to the shell thereby forming a sealed prosthesis.

24. The method of claim 23, wherein the light is supplied by a laser.

25. The method of claim 23, wherein the patch and the shell comprise high temperature vulcanization silicone.

26. The method of claim 23, wherein the patch and the shell comprise room temperature vulcanization silicone.

27. The method of claim 23, wherein the shell and patch have a thickness between about 0.20 inches and about 0.0005 inches.

28. The method of claim 23, wherein the prosthesis is a mammary prosthesis.

29. The method of claim 23, wherein the shell is made from room temperature vulcanization silicone and the patch is made from high temperature vulcanization silicone.

30. The method of claim 23, wherein the shell is made from high temperature vulcanization silicone and the patch is made from room temperature vulcanization silicone.

31. The method of claim 23, further comprising providing a light absorbing substance disposed in the overlap region and wherein the light absorbing substance absorbs light of the selected wavelength, thereby heating the surfaces of the patch and shell in contact with each other.

32. The method of claim 23, further comprising providing a light absorbing material disposed on either the surface of the patch or the surface of the shell in the overlap between the patch and shell.

33. The method of claim 23, wherein the light absorbing material is integrated into an absorber patch that is disposed in the overlap.

34. The method of claim 23, wherein the light absorbing substance is carbon black.

35. The method of claim 23, wherein the shell and the patch comprise a thermoplastic polymer.

36. The method of claim 23, wherein the shell and the patch comprise a thermoset polymer.

37. The method of claim 23, wherein the shell and patch comprise polyurethane.

* * * * *